United States Patent [19]

Sasaki et al.

[11] Patent Number: 4,624,950
[45] Date of Patent: Nov. 25, 1986

[54] METHOD FOR TREATING ATHEROSCLEROSIS HYPERLIPIDEMA, LIPID DEPOSITION ON ARTERIAL WALLS, OR RAISING THE RATIO OF HIGH DENSITY LIPOPROTEIN CHOLESTEROL TO TOTAL CHOLESTEROL IN SERUM

[75] Inventors: Tadashi Sasaki, Tokyo; Yoshihiro Fujikawa, Funabashi; Ryozo Sakoda, Kashiwa; Mitsuaki Sakashita, Urawa; Morihide Hibi, Sagamihara, all of Japan

[73] Assignee: Nissan Chemical Industries Ltd., Tokyo, Japan

[21] Appl. No.: 640,120

[22] Filed: Aug. 13, 1984

[30] Foreign Application Priority Data

Aug. 19, 1983 [JP] Japan ................................. 58-152339
Jan. 26, 1984 [JP] Japan ................................. 59-13044

[51] Int. Cl.⁴ .................... A61K 31/38; A61K 31/395
[52] U.S. Cl. ......................................... 514/222; 544/8
[58] Field of Search ..................... 544/8; 424/246; 514/222

[56] References Cited

FOREIGN PATENT DOCUMENTS 118992  5/1976  German Democratic Rep. .... 544/8

OTHER PUBLICATIONS

Huisgen et al, Chem. Ber. 100, 1602–1615, (1967), at p. 1614.
Augustin et al, C.A., vol. 81, 1974, 84:136119a.
Zeitschrift fuer Chemie, 14, 1974, p. 270, M. Augustin et al.
Die Pharmazie, 28, 1973, G. Würbach et al.

*Primary Examiner*—Henry R. Jiles
*Assistant Examiner*—J. G. Mullins
*Attorney, Agent, or Firm*—Oblon, Fisher, Spivak, McClelland, & Maier

[57] ABSTRACT 3,5-Dimethyl-4,6-diphenyl-tetrahydro-2H-1,3,5-thiadiazine-2-thione having the formula:

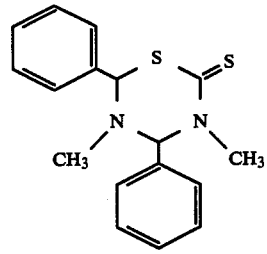

as an antiatherosclerotic agent.

4 Claims, No Drawings

METHOD FOR TREATING ATHEROSCLEROSIS HYPERLIPIDEMA, LIPID DEPOSITION ON ARTERIAL WALLS, OR RAISING THE RATIO OF HIGH DENSITY LIPOPROTEIN CHOLESTEROL TO TOTAL CHOLESTEROL IN SERUM

The present invention relates to an antiatherosclerotic agent. More particularly, the present invention relates to 3,5-dimethyl-4,6-diphenyl-tetrahydro-2H-1,3,5-thiadiazine-2-thione having the formula:

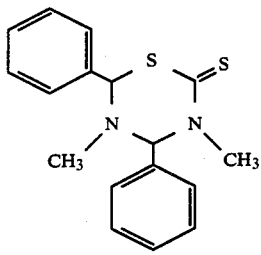

useful as an active antiatherosclerotic agent.

Hyperlipidemia (hyperlipemia) is regarded as a major risk factor for the atherosclerosis. Heretofore, a number of antihyperlipidemic agents have been studied. Therapeutic agents in this field are likely to be used for an extended period of time in view of the nature of the diseases, and they are required to be highly safe. However, with respect to nicotinic acid and its derivatives, or clofibrate and its derivatives, which have been widely used as antihyperlipidemic agents, various subsidiary ill effects have been reported, and they can hardly be accepted as satisfactory therapeutic agents. For instance, with respect to nicotinic acid and its derivatives, it has been reported that they will bring about e.g. flashing or gastroenteric troubles. With respect to clofibrate and its derivatives, it is known that they will bring about e.g. myalgia or hepatic insufficiency, and they are likely to lead to gallstone formation. Further, it has been reported that clofibrate brings about hepatic carcinoma on animal experiments. [D. J. Svoboda and D. L. Azarnoff, Cancer Res., 39, 3419 (1979)]

In addition to the question of the safety, there has been a progress in the study of the pharmacological activities. Reflecting the progress in the recent years in the study of the lipid metabolism, particularly in the study of the functional mechanism of serum lipoprotein as a transporter of serum lipid, an attention about the effect of the drug has been drawn not only to the activity of the drug to reduce the lipid concentration in serum but also to the effect to the lipoprotein. Serum cholesterol constitutes the lipoprotein together with triglyceride, phospholipid and apoprotein. This lipoprotein is generally classified into Cyromicron, VLDL (very low density lipoprotein), LDL (low density lipoprotein) and HDL (high density lipoprotein) depending upon the difference in the specific gravity. Among these, Cyromicron, VLDL and LDL are believed to be the lipoproteins which induce atherosclerosis. Whereas, HDL is believed to have functions to transport cholesterol from peripheral blood vessels to a liver, to form a cholesterol ester or to contribute to the catabolism of triglyceride, and thus serves for the prevention and regression of the atherosclerosis. Accordingly, for an antihyperlipidemic agent to be developed, it is desired that such an agent has not only the function to reduce the total value of serum cholesterol, but also the functions to reduce LDL-cholesterol and to increase HDL-cholesterol. A therapeutic agent having both of such functions, exhibits an effect to prevent lipid deposition on arterial walls, and thus serves as an antiatherosclerotic agent.

The synthesis of 3,5-dimethyl-4,6-diphenyl-2H-1,3,5-thiadiazine-2-thione useful as a therapeutic agent of the present invention, is disclosed in Chem. Ber., 100, 1602 (1967) and Zeitschrift fuer Chemie, 14, 270 (1974). However, no application of this compound to medical or pharmaceutical agents has been known. Further, various derivatives having a basic structure of tetrahydro-2H-1,3,5-thiadiazine-2-thione have been synthesized and have been known as being useful as fungicides or animal food additives (nutrients). However, nothing has been known with respect to their antihyperlipidemic effect and antiatherosclerotic effect.

As a result of extensive researches for compounds having antiatherosclerotic effects, the present inventors have found that the above-mentioned 3,5-dimethyl-4,6-diphenyl-tetrahydro-2H-1,3,5-thiadiazine-2-thione (hereinafter referred to simply as "the compound of the formula I") has excellent antihyperlipidemic effect and is particularly effective not only to reduce LDL-cholesterol and increase HDL-cholesterol, but also to prevent the lipid deposition on arterial walls. On the basis of this discovery, it has been found that the compound of the formula I is useful as an active ingredient for an antiatherosclerotic agent. The anti-atherosclerotic agent is effective as a preventive and curative pharmaceutical composition for ischemic circulatory organs diseases such as myocardial infarction, heart attack, cerebral infarction, hypertension or thrombus. Further, it has been found that the compound of the formula I is a highly safe compound which does not bring about side effects to liver, such as hepatomegaly or hepatic insufficiency.

The pharmaceutical composition of the present invention comprises an effective amount of the compound of the formula I and a pharmaceutically acceptable carrier. The effective amount is usually at least 5% by weight, based on the total composition. As the pharmaceutically acceptable carrier, there may be mentioned a pharmaceutically acceptable binder such as a syrup, gum arabic, gelatin, sorbitol, tragacanth gum or polyvinylpyrrolidone (molecular weight of e.g. about 25,000); an excipient such as lactose, sugar, corn starch, calcium phosphate, sorbitol or glycine; a lubricant such as magnesium stearate, talc, polyethylene glycol or silica; or a disintegrator such as potato starch. By properly selecting the carrier, the pharmaceutical composition of the present invention may be formulated into powders, granules, tablets or capsules. It is preferably administered orally. However, the manner of administration is not restricted to oral administration, and non-oral administration may be employed.

The daily dose of the compound of the formula I is from 0.01 to 3.0 g, preferably from 0.1 to 1.5 g, for an adult. It is administered from once to three times per day. The dose may of course be varied depending upon the age, the weight or the condition of illness of the patient. Now, the usefulness of the compound of the formula I as an antiatherosclerotic agent will be shown by tests. In the following tests, the fractionation of lipoproteins was conducted by a dextran sulfate-$MgCl_2$ precipitation method.

Cholesterol in serum was measured by means of a cholesterol measuring kit (Cholesterol C-Test Wako, manufactured by Wako Junyaku Co., Ltd.), and cholesterol in HDL was measured by means of NC Hi-Set, manufactured by Nippon Chemiphar Co., Ltd. The quantitative analysis of triglyceride was conducted by means of a triglyceride measuring kit (Triglyceride C-II-Test Wako, manufactured by Wako Junyaku Co., Ltd.).

In the following Tables, cholesterol is referred to as "Chol", and triglyceride is referred to as "TG".

Further, the change rate in the following Tables, was calculated by the following equation.

$$\text{Change rate}(\%) = (A - B/A) \times 100$$

where A is the amount of serum lipids (mg/dl) of the control group, and B is the amount of serum lipids (mg/dl) of the group to which the therapeutic agent was administered.

TEST 1

The antihyperlipidemic activity in emulsion-induced hyperlipidemic rats

Male S.D. rats weighing 80–90 g (4 weeks old) were used. They were divided into groups of 5 to 6 rats each. The test compounds suspended in 0.5% CMC-Na(carboxymethyl cellulose sodium salt) were given to the rats in a daily dose of 4 ml/kg via stomach tube every 10:00 a.m. After 30 min., lipids emulsion having the following composition was orally given to the rats in an amount of 2.5 ml per rat. During the experimental period of 3 days, the rats were fed on a standard commercial diet and water ad libitum. At the end of the period, the rats were fasted for 16 hours and then blood samples were obtained from inferior vena cava. The total cholesterol and triglyceride, and HDL cholesterol were measured. The results are shown in Table 1.

| Composition of emulsion: | |
|---|---|
| Cholesterol | 22.5 g |
| Cholic acid sodium salt | 10.0 g |
| Sucrose | 90.0 g |
| Olive oil | 150.0 g |
| Water | × ml |
| Final volume | 300.0 ml |

TABLE 1

| | | Serum lipid | | |
|---|---|---|---|---|
| Test compounds | Dose mg/kg | Total Chol mg/dl | HDL-Chol mg/dl | TG mg/dl |
| Compound of formula I | 300 | 145 (−45.0) *2 | 22.1 (+80.6) | 97.4 (−36) |
| Clofibrate *1 | 300 | 96.4 (−63.5) | 16.8 (+37.0) | 87.7 (−42.7) |
| Control | — | 266.8 | 12.3 | 153.0 |

*1 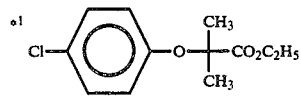

*2 Change rate (%)

TEST 2

The antihyperlipidemic activity in Triton-induced hyperlipidemic rats

Male S.D. rats weighing 230–250 g (7 weeks old) were divided into groups of 5 rats each and injected with a physiological saline solution of Triton Wr-1339 in a dose of 250 mg/kg (5 ml/kg) i.v. through the tail vein. After 24 hours (method A) or 43 hours (method B), blood samples were taken from the inferior vena cava with the animals. The test compounds suspended in 0.5% CMC-Na were given to the rats in an amount of 2 ml/kg via stomach tube 1 hour before and 5 hours after (in the case of method A) or 1 hour before and 23 hours after (in the case of method B) the injection of Triton solution. Control rats received the same volume of the vehicle. The animals were fasted during the experimental period. The total cholesterol and triglyceride in the serum were measured. The results are shown in Table 2.

TABLE 2

| Test compounds | Dose mg/kg | Change rate (%) after 24 hours | | Change rate (%) after 43 hours | |
|---|---|---|---|---|---|
| | | Chol | TG | Chol | TG |
| Compound of the formula I | 150 | −6.0 | +21.8 | −43.5 | −65.7 |
| Clofibrate *1 | 300 | −5.0 | +89.7 | −0.5 | +150.1 |
| Clinofibrate *2 | 150 | −21.0 | −33.0 | −38.0 | −52.0 |

*1 As identified in Table 1.

*2 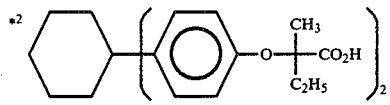

As is evident from Table 2, the compound of the formula I showed a distinct lipid reducing activity in the case of method B although no lipid reducing activity was observed in the case of method A.

TEST 3

The antihyperlipidemic activity in cholesterol-fed hyperlipidemic rats

Male S.D. rats weighing 80–90 g (30 days old) were divided into groups of 5 rats each. The test compounds suspended in 0.5% CMC-Na were given to the rats in a daily dose of 0.4 ml per 100 g rat via stomach tube every 10:00 a.m. for 7 or 14 days. Control groups were given an equal volume of the vehicle. During the experimental period, the animals were fed on a 1% cholesterol diet (powdered form) prepared by the method of Tensho et al. [Yakugaku Zasshi, 92, 878 (1972)]. At the end of the period, the animals were fasted for 16 hours and then blood samples were obtained from inferior vena cava. The total cholesterol, triglyceride and HDL cholesterol in serum were measured. After sacrificed, the livers were excised, washed with physiological saline, blotted on filter paper and weighed. The degree of hepatomegaly was calculated by the following equation.

$$\text{Degree of hepatomegaly}(\%) = (D - C/C) \times 100$$

where C is the liver weight (g) per 100 g body weight in the control animal, and D is the liver weight (g) per 100 g body weight in the drug treated animal.

The results on the 7th day are shown in Table 3, and the results on the 14th day are shown in Table 4.

TABLE 3

| Test compounds | Dose mg/kg | 7th day Serum lipid Total-Chol mg/dl | HDL-Chol mg/dl | TG mg/dl | Degree of hepato-megaly (%) |
|---|---|---|---|---|---|
| Compound (I) | 150 | 385 (−11.7)*2 | 17.3 (−4.4) | 66.2 (−46.1) | +12.0 |
|  | 100 | 294.7 (−32.4) | 19.2 (+6.1) | 92.7 (−24.5) | ±0 |
|  | 50 | 289.8 (−33.6) | 18.1 (0) | 104.0 (−15.3) | +2.0 |
|  | 10 | 421.7 (−3.3) | 15.8 (−12.7) | 105.9 (−13.8) | +4.0 |
| Clofibrate*1 | 150 | 332.2 (−23.8) | 11.8 (−34.8) | 111.8 (−9.0) | +20.0 |
|  | 50 | 417.5 (−4.3) | 14.4 (−20.4) | 133.5 (+8.7) | +6.0 |
| Control | — | 426.2 | 18.1 | 112.8 | — |

*1 As identified in Table 1.
*2 Change rate (%)

TABLE 4

| Test compounds | Dose mg/kg | 14th day Serum lipid Total-Chol mg/dl | HDL-Chol mg/dl | TG mg/dl | Degree of hepato-megaly (%) |
|---|---|---|---|---|---|
| Compound (I) | 150 | 228.6 (−60.9)*2 | 21.5 (+147.1) | 77.1 (−53.8) | +5.3 |
|  | 100 | 271.3 (−53.7) | 24.9 (+186.2) | 92.2 (−44.8) | +10.5 |
|  | 50 | 389.2 (−33.5) | 20.5 (+135.6) | 87.7 (−47.5) | +1.8 |
|  | 10 | 336.5 (−42.5) | 20.0 (+129.9) | 92.5 (−44.6) | +5.3 |
| Clofibrate*1 | 150 | 420.0 (−28.3) | 15.8 (+68.1) | 117.7 (−29.8) | +22.8 |
|  | 50 | 418.4 (−28.5) | 9.4 (+8.0) | 116.6 (−30.1) | +8.8 |
| Control | — | 585.4 | 8.7 | 166.9 | — |

*1 As identified in Table 1
*2 Change rate (%)

The compound of the formula I showed a strong lipid reducing activity and HDL-cholesterol increasing activity on the 14th day although such activities are not distinct very much on the 7th day. Further, it was found to have no hepatomegaly.

TEST 4

The effect of the compound of the formula I on experimental atherosclerosis in rabbits induced by cholesterol diet Twenty-five male rabbits weighing 1.8–2.0 kg were used. They were fed with basic chow (Nippon clea, CR-3) for a stabilizing period of 5 days. After this period, they were fed with the chow containing 1% cholesterol, 100 g per head a day for a week (7 days) and plasma cholesterol was measured using a blood sample collected from acuricle vein.

According to the results of cholesterol values measured, 14 animals of high cholesterol plasma level were selected. They were divided into two groups to have nearly equal means and S.D. values of plasma cholesterol. One group of 7 rabbits was fed with the chow containing 1% cholesterol and another group of 7 rabbits was fed with the chow containing 1% cholesterol and 0.1% compound of the formula I in an amount of 100 g per head a day for 8 weeks.

Rabbits were sacrificed at the end of 8 weeks. Aortic arch and thoracic aorta were excised, and macroscopical changes were examined using the Sudan III stain method. According to the results of gross observation of the internal surface stained by Sudan III, the ratios of the atherosclerotic plaque area (the area stained by Sudan III) to the whole internal surface area were calculated. The ratio of inhibition of atherosclerosis of the compound of the formula I was obtained by comparing the average value with the value of the control.

TABLE 5

|  | Atherosclerotic plaque area stained by Sudan III (%) | | |
|---|---|---|---|
|  | Aortic arch | Thoracic aorta | Total aorta |
| Control (E) | 90.1 | 34.1 | 48.0 |
| Treated with compound (I) (F) | 77.7 | 11.0 | 26.3 |
| Ratio of inhibition of atherosclerosis (Ratio of Improvement) (G) (%)* | 13.8 | 67.7 | 45.3 |

$$*G = \frac{E - F}{E} \times 100 \ (\%)$$

It was confirmed that the compound of the formula I inhibits experimental atherosclerosis on rabbits raised with 1% cholesterol diet.

TEST 5

The activities against serum lipid, the degree of hepatomegaly and the hepatic drug metabolizing systems of normal rats Male S.D. rats (6 weeks old) were divided into groups of 5 rats each. The test compounds suspended in 5% gum arabic were given to the rats once a day for seven days in a daily dose of 300 mg/kg. Then, the rats were fasted for one day, blood samples were taken, and the total cholesterol, triglyceride, HDL-cholesterol in the serum were quantitatively analyzed. Further, the liver weight was measured, and the degree of hepatomegaly was determined by comparing the weight ratio per 100 g of the body weight with that of the control group. Furthermore, GOT and GPT values were measured, and the activities of cytochrome P-450 and glutathione related enzymes were also measured. These values were compared with those of the control groups to investigate any abnormality. The results are shown in Table 6.

TABLE 6

| Test compounds | Dose mg/kg | Serum lipid Total-Chol mg/dl | HDL-Chol mg/dl | TG mg/dl | Degree of hepato-megaly (%) |
|---|---|---|---|---|---|
| Compound (I) | 300 | 39.2 (−16.2)-*2 | 29.2 (−1.0) | 37.5 (−21.0) | +7.0 |
| Clofibrate*1 | 300 | 20.6 (−56.0) | 11.0 (−62.7) | 39.2 (−17.5) | +72.0 |
| Control | — | 46.8 | 29.5 | 47.5 | — |

*1 As identified in Table 1.
*2 Change rate (%)

It is evident from Table 6 that the compound of the formula I brings about no substantial hepatomegaly in the normal rats, and it ramarkably reduces LDL-cholesterol. No hepatic insufficiency was observed from the GOT and GPT values. Further, no abnormalities were observed with respect to the activity against cytochrome P-450 or other liver microsome drug metabolizing systems, and against glutathione related enzymes.

TEST 6

Mutagenicity test

The mutagenicity was tested by using *Escherichia coli* (WP2UVrA) and Salmonella (TA98, TA100, TA1535 and TA1538) in the absence or presence of a drug metabolizing enzymes S-9 mix of rat liver. The compound of the formula I did not show any mutagenicity up to a concentration as high as 5000 μg/Plate, thus indicating that it is a highly safe compound.

TEST 7

Acute toxicity test

The test compounds suspended in 0.5% CMC-Na were administered p.o. or injected i.p. to male ddY mice. The acute toxicity was dertermined based on the mortality after seven days. The compound of the formula I showed no toxicity up to the dose of 8,000 mg/kg in the case of the oral administration and up to the dose of 4,000 mg/kg in the case of the abdominal administration, thus indicating that it is a safe compound having a low acute toxicity.

Now, examples will be given for various formulations containing the compound of the formula I.

Tablets

| Composition (4,000 tablets) | |
|---|---|
| Compound of the formula (I) | 500 (g) |
| Potato starch | 334 |
| Carboxymethyl cellulose | 87.5 |
| Polyvinyl alcohol | 61 |
| Magnesium stearate | 17.5 |
| | 1,000 |

The above ingredients in the respective amounts were introduced into a twin shell mixer and uniformly mixed. This power mixture was tableted by a direct compression method to obtain tablets having a weight of 250 mg per tablet.

Capsules

| Composition (10,000 capsules) | |
|---|---|
| Compound of the formula I | 2,500 (g) |
| Potato starch | 400 |
| Magnesium stearate | 100 |
| | 3,000 |

The above ingredients in the respective amounts were introduced into a twin shell mixer and uniformly mixed. This powder mixture was packed in hard gelatin capsules in an amount of 300 mg per capsule.

Powder

| Composition: | |
|---|---|
| Compound of the formula I | 200 (g) |
| Lactose | 800 |
| | 1,000 |

The above ingredients in the respective amounts were introduced into a twin shell mixer and uniformly mixed to obtain a powder.

We claim:

1. A method of reducing the incidence or severity of atherosclerosis in a mammal comprising administering to said mammal an amount effective to reduce the incidence or severity of atherosclerosis of a pharmaceutical composition comprising 3,5-dimethyl-4,6-diphenyl-tetrahydro-2H-1,3,5-thiadiazine-2-thione having the formula:

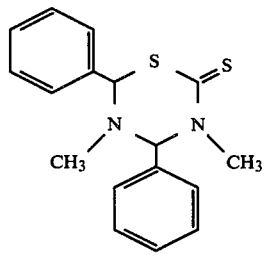

and a pharmaceutically acceptable carrier.

2. A method of treating hyperlipidemia in a mammal in need of such treatment comprising administering to said mammal an antihyperlipidemically effective amount of a pharmaceutical composition comprising 3,5-dimethyl-4,6-diphenyl-tetrahydro-2H-1,3,5-thiadiazine-2-thione having the formula:

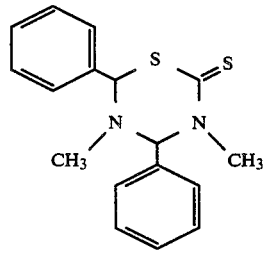

and a pharmaceutically acceptable carrier.

3. A method of reducing lipid deposition on the arterial walls of a mammal comprising administering to said mammal an amount effective to reduce the lipid deposition on the arterial walls of a pharmaceutical composition comprising 3,5-dimethyl-4,6-diphenyl-tetrahydro-2H-1,3,5-thiadiazine-2-thione having the formula:

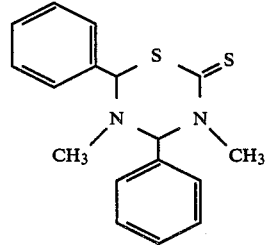

and a pharmaceutically acceptable carrier.

4. A method of raising the ratio of high density lipoprotein cholesterol in serum to total cholesterol in serum in a mammal in need of such raising of ratio comprising administering to said mammal a ratio raising effective amount of a pharmaceutical composition comprising 3,5,-dimethyl-4,6-diphenyl-tetrahydro-2H-1,3,5-thiadiazine-2-thione having the formula:

9
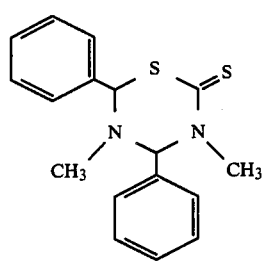
and a pharmaceutically acceptable carrier.
* * * * *
10
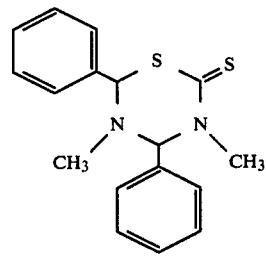
and a pharmaceutically acceptable carrier.
* * * * *